(12) United States Patent
Wiley

(10) Patent No.: US 11,974,946 B2
(45) Date of Patent: May 7, 2024

(54) SELF-CONTAINED OCULAR SURGERY INSTRUMENT

(71) Applicant: William F. Wiley, Chagrin Falls, OH (US)

(72) Inventor: William F. Wiley, Chagrin Falls, OH (US)

( * ) Notice: Subject to any disclaimer, the term of this patent is extended or adjusted under 35 U.S.C. 154(b) by 190 days.

(21) Appl. No.: 17/243,006

(22) Filed: Apr. 28, 2021

(65) Prior Publication Data

US 2021/0244873 A1 Aug. 12, 2021

Related U.S. Application Data

(62) Division of application No. 16/141,266, filed on Sep. 25, 2018, now Pat. No. 10,994,061.

(Continued)

(51) Int. Cl.
*A61F 9/007* (2006.01)
*A61F 2/16* (2006.01)
(Continued)

(52) U.S. Cl.
CPC ........ *A61F 9/00763* (2013.01); *A61F 2/1662* (2013.01); *A61F 9/00736* (2013.01);
(Continued)

(58) Field of Classification Search
CPC ........ A61B 2217/005; A61B 2217/007; A61F 2/1662; A61F 9/00736; A61F 9/00763;
(Continued)

(56) References Cited

U.S. PATENT DOCUMENTS

| 4,757,426 A | 7/1988 | Scheller |
|---|---|---|
| 6,183,488 B1 | 2/2001 | Ross et al. |

(Continued)

FOREIGN PATENT DOCUMENTS

| WO | WO 97/41784 A1 | 11/1997 |
|---|---|---|
| WO | WO 2011/154971 A1 | 12/2011 |
| WO | WO 2014/152405 A1 | 9/2014 |

OTHER PUBLICATIONS

PCT International Search Report and Written Opinion for International Application No. PCT/US2018/052620, dated Feb. 19, 2019, 12 pages.

(Continued)

*Primary Examiner* — Jocelin C Tanner
(74) *Attorney, Agent, or Firm* — DeWitt LLP

(57) ABSTRACT

A self-contained ocular surgery instrument, including a power module having a body presenting a mating coupler and including a compressed gas supply; a fluid reservoir; an aspiration pump; an aspirated material reservoir and a control panel. The mating coupler is structured to receive and couple to at least one module that facilitates performance of an eye surgery task. The compressed gas supply is coupled to the aspiration pump and the aspirated material reservoir is in fluid communication with the aspiration pump to receive aspirated material from the mating coupler. The fluid reservoir is in fluid communication with the mating coupler such that fluid is supplied under pressure to the mating coupler and thus to the at least one module that facilitates performance of an eye surgery task. The control panel is in controlling communication with the compressed gas supply, the aspiration pump and the aspirated material reservoir.

8 Claims, 2 Drawing Sheets

Related U.S. Application Data

(60) Provisional application No. 62/563,408, filed on Sep. 26, 2017.

(51) Int. Cl.
*A61F 9/008* (2006.01)
*A61M 1/00* (2006.01)

(52) U.S. Cl.
CPC ............... *A61F 9/008* (2013.01); *A61M 1/74* (2021.05); *A61M 1/772* (2021.05); *A61M 1/774* (2021.05); *A61B 2217/005* (2013.01); *A61B 2217/007* (2013.01); *A61F 2009/0087* (2013.01); *A61M 2205/07* (2013.01); *A61M 2210/0612* (2013.01)

(58) Field of Classification Search
CPC ... A61F 9/008; A61F 2009/0087; A61M 1/74; A61M 1/772; A61M 1/774; A61M 2205/07; A61M 2210/0612
See application file for complete search history.

(56) References Cited

U.S. PATENT DOCUMENTS

| | | | |
|---|---|---|---|
| 6,358,260 B1 | 3/2002 | Ross et al. | |
| 6,425,905 B1 | 7/2002 | Guimaraes et al. | |
| 6,663,644 B1 | 12/2003 | Ross et al. | |
| 7,311,700 B2 | 12/2007 | Guimaraes et al. | |
| 7,645,291 B2 | 1/2010 | Ross et al. | |
| 7,658,774 B2 | 2/2010 | Ross et al. | |
| 8,070,764 B2 | 12/2011 | Ross et al. | |
| 8,333,778 B2 | 12/2012 | Smith | |
| 8,424,362 B2 | 4/2013 | Hajishah et al. | |
| 8,597,277 B2 | 12/2013 | Lenker | |
| 8,923,768 B2 | 12/2014 | Ma et al. | |
| 8,986,242 B2 | 3/2015 | Auld et al. | |
| 8,998,983 B2 | 4/2015 | Auld | |
| 9,125,731 B2 | 9/2015 | Ross et al. | |
| 9,370,611 B2 | 6/2016 | Ross et al. | |
| 9,393,370 B2 | 7/2016 | Auld et al. | |
| 9,693,895 B2 | 7/2017 | Auld et al. | |
| 9,764,088 B2 | 9/2017 | Huculak et al. | |
| 9,999,710 B2 | 6/2018 | Ross et al. | |
| 10,029,052 B2 | 7/2018 | Auld et al. | |
| 2004/0167480 A1* | 8/2004 | Bos | A61F 9/0008 604/289 |
| 2005/0152759 A1 | 7/2005 | Allemann et al. | |
| 2008/0114290 A1 | 5/2008 | King | |
| 2008/0300531 A1* | 12/2008 | Gills, Jr. | A61F 9/00736 604/22 |
| 2010/0280435 A1 | 11/2010 | Raney | |
| 2011/0144567 A1 | 6/2011 | Sorensen et al. | |
| 2011/0264102 A1* | 10/2011 | Cole | A61F 9/00745 606/107 |
| 2012/0065655 A1 | 3/2012 | Ross et al. | |
| 2012/0296423 A1 | 11/2012 | Caffey | |
| 2013/0085482 A1 | 4/2013 | Van Valen et al. | |
| 2013/0197531 A1* | 8/2013 | Boukhny | A61F 9/00736 606/107 |
| 2014/0005681 A1 | 1/2014 | Gee et al. | |
| 2014/0121608 A1* | 5/2014 | Perkins | A61F 9/00736 604/272 |
| 2014/0276377 A1* | 9/2014 | Chang | A61F 9/00736 604/35 |
| 2014/0276901 A1 | 9/2014 | Auld | |
| 2014/0330204 A1 | 11/2014 | Huculak et al. | |
| 2014/0358155 A1 | 12/2014 | DeBoer | |
| 2015/0045806 A1* | 2/2015 | Urich | A61M 1/774 606/107 |
| 2016/0220751 A1 | 8/2016 | Mallough | |
| 2016/0346122 A1 | 12/2016 | Charles | |
| 2017/0071787 A1 | 3/2017 | Canelli et al. | |
| 2017/0224888 A1* | 8/2017 | Hickey | A61M 3/0279 |
| 2019/0015252 A1* | 1/2019 | Lake | A61F 9/00825 |

OTHER PUBLICATIONS

Application and File History for U.S. Appl. No. 16/141,266, filed Sep. 25, 20218. Inventor: William F. Wiley.
Supplementary European Search Report for European Application No. EP 18 86 2171, dated May 27, 2021, 7 pages.

* cited by examiner

SELF-CONTAINED OCULAR SURGERY INSTRUMENT

CROSS-REFERENCE TO RELATED APPLICATION

This application is a divisional of U.S. application Ser. No. 16/141,266, filed Sep. 25, 2018 entitled "Self-Contained Ocular Surgery Instrument" which application claims the benefit of U.S. Provisional Application No. 62/563,408, filed Sep. 26, 2017, entitled "Self-Contained Ocular Surgery Instrument," all of which are hereby incorporated herein in its entirety by reference.

TECHNICAL FIELD

Embodiments of the invention relate generally to the field of ocular surgery. More particularly, embodiments of the invention relate to handheld instruments for ocular surgery.

BACKGROUND

Cataracts, a leading cause of vision loss and even blindness worldwide, occur when the natural crystalline lens of the eye becomes cloudy or opacified. Cataract surgery is commonly performed by the method of phacoemulsification. Phacoemulsification is a commonly practiced ocular surgical procedure for removing cataracts.

Cataracts are caused by protein aggregation and accumulation in the natural crystalline lens, causing light scattering. The interference with the passage of light through the natural crystalline lens causes images to become cloudy and distorted, thereby diminishing visual acuity. Severe diminishment of visual acuity from cataracts can lead to an increase in auto accidents, falls, and other social problems. Generally, in the United States, cataract surgery is performed well prior to severe reduction in vision as a consequence of the cataract.

Therefore, several surgical procedures, including phacoemulsification, have been developed to treat cataracts to restore lost vision. Generally, cataract surgical procedures are performed to remove the clouded natural crystalline lens and implant an artificial intraocular lens to replace the focusing power of the removed natural lens.

Phacoemulsification is performed with a hand-held instrument that includes an ultrasonically vibrating needle like tip, an aspiration tube and a conduit to supply a balanced salt solution to replace fluid that is removed from the eye by aspiration. The phacoemulsification instrument is coupled to a console by various tubing as well as an electrical supply. The console provides power for the ultrasonic vibrating mechanism, a source of suction to accomplish aspiration and a source of fluid under pressure to replace fluid removed from the eye by aspiration and to maintain the anterior chamber during the procedure.

New developments in cataract surgery have made the need for ultrasonic power supply less necessary as instruments utilizing femtosecond laser are being used to section the crystalline lens of the eye into small pieces to facilitate removal of the lens.

The conventional phacoemulsification procedure emulsifies the affected lens with the use of an ultrasonic hand-held device. Typically, the ultrasonic device includes a needle like tip, which is through an incision made near the outer edge of the cornea of the eye. Once inserted, the needle tip vibrates ultrasonically to fragment the lens for removal by aspiration. After the natural lens is fragmented and substantially removed, an artificial intraocular lens is implanted through the incision to replace the natural lens and its focusing power.

In addition to the needle tip, the hand-held device generally includes an irrigation sleeve and an aspiration channel. The aspiration channel is housed within a hollow cross sectional area of the needle tip and is coupled to a source of suction to aspirate fluid and fragmented tissue during the procedure. The irrigation sleeve surrounds the needle tip and introduces liquid, typically a balanced salt solution to aid in flushing and aspirating lens fragments and to replace fluid withdrawn or lost from the eye chamber. Phacoemulsification procedures have proven highly effective, however, the requirement that the handheld phacoemulsification instrument be tethered to a console can limit the surgeon's mobility and may increase the difficulty of the procedure.

Vitrectomy is another ophthalmic surgical procedure that is performed. Vitrectomy involves the partial or complete removal of the vitreous body which occupies the largest cavity of the eye. There are a large number of reasons why vitrectomy may be necessary or desirable. These reasons include the presence of a diabetic vitreous hemorrhage, the existence of a retinal detachment, the presence of an epiretinal membrane, the existence of a macular hole, the presence of proliferative vitreoretinopathy, endophthalmitis, the presence of an intraocular foreign body and the necessity to retrieve a lens nucleus following complicated cataract surgery. Generally, the vitreous body is removed to provide a better access to the retina for repairers of the retina. However, as apparent from the above list other reasons exist as well.

Typically in vitrectomy the dilated eye is entered through an incision made through the pars plana and through the sclera. The sclera is the white structural wall of the eye. The pars plana is a part of the far peripheral retina and choroid within the eye. While viewing the interior of the eye through a surgical microscope and a specialized lens the surgeon makes use of a vitrectomy probe, called a vitrector, to section and remove the gel-like vitreous body. During the procedure, additional openings in the wall of the eye are made to provide illumination within the eye into place various other instruments in the eye to assist in surgery. Thus the surgeon may utilize a light pipe for illumination, forceps to peel membranes or scar tissue, silicone tripped drainage needles to drain fluid from within the eye or an intraocular laser probe to assist in sealing around retinal tears or to treat abnormal blood vessels found in the eye. Conventional vitrectomy probes are typically tethered to a console which provides vacuum and fluid replacement and a source of energy to operate the cutter of the vitrectomy probe.

Following cataract surgery an intraocular lens implant (IOL) is typically inserted into the eye to substitute for the focusing power of the natural lens which has been removed to provide focused vision for the patient. Many IOLs that are used are foldable. That is the IOL can be folded or rolled and inserted into the eye through a cannula like injector. Typically these IOL injectors require the surgeon to use both hands to place the foldable IOL. A first hand is used to hold the injector in position so that the cannula is within the eye and the lens capsule. A secondhand is then used to manipulate a plunger or slide that pushes the foldable IOL through the cannula. The need to use both hands to operate the IOL injector can be limiting to the surgeon.

In view of the above, there is still room for improvement in the ophthalmic surgery arts related to cataract extraction.

SUMMARY

Embodiments of the present invention include a self-contained handheld instrument for performing eye surgical procedures without the necessity of being tethered to a console that provides sources of electrical power, suction and fluid replacement. These embodiments overcome many of the above discussed concerns.

An example embodiment of the self-contained handheld instrument includes an onboard compressed gas supply that drives aspiration as well as fluid replacement. The handheld instrument also includes a supply of balanced salt solution or another liquid to replace fluid aspirated from the eye. Example embodiments of the self-contained handheld instrument may include a venturi pump or a compressed gas driven piston or turbine pump to provide for aspiration of lens fragments as well as other power for operating the instrument.

According to an example embodiment of the invention, all power to operate the instrument is the provided by compressed gas. According to another example embodiment of the invention, battery power may be utilized. However electronics tend not to stand up well to sterilization procedures.

Another example embodiment of the invention is adapted for use in other surgical procedures such as vitrectomy and a similarly powered by an onboard compressed gas supply.

Another example embodiment further includes a module to support lens insertion. The lens insertion module may be coupled to the power module via a mating coupler. The lens insertion module may include a cannula structure that receives the foldable or rolled IOL therein and a slide or plunger structure that can be advanced within the cannula to direct the foldable or rolled IOL into the eye, for example, into the lens capsule. According to an example embodiment of the invention the slide or plunger structure is advanced by pressure provided by compressed gas and a coupled piston is slidably movable within the cannula to advance the foldable IOL. Accordingly, the advancement and insertion of the IOL can be controlled by the surgeon using only one hand by holding the device and controlling a switch or valve which can be manipulated by a single finger, for example. The controlling switch or valve is operably coupled to the compressed gas supply and selectively releases the compressed gas.

According to another example embodiment, the invention includes a module to support vitrectomy. The vitrectomy module may be coupled to the power module via a mating coupler. The vitrectomy module generally includes a cutting probe and aspiration portion and a fluid replacement portion. The cutting probe is similar to vitrectors known to those of skill in the art and may be available in multiple sizes, for example, 20 gauge, 25 gauge and 27 gauge. The aspiration portion and fluid replacement portion are similar to those otherwise utilized in vitrectomy.

According to another example embodiment the invention may include a power module portion including the compressed gas supply and supply of balanced salt solution and three interchangeable modules that are adapted respectively for phacoemulsification, vitrectomy and lens insertion after crystalline lens removal.

According to another example embodiment of the invention, the container for supplying balanced salt solution to accommodate 50 to 70 mL of solution. According to another example embodiment, the fluid supply may include a viscoelastic solution as an alternative to a balanced salt solution. It is expected that the use of a viscoelastic solution as a medium instead of balanced salt solution will facilitate safe and efficient aspiration of the cortex and nucleus of the crystalline lens. The application of viscoelastic may reduce the required fluid volume to perform a lens extraction procedure to as little as a few milliliters as compared to 50 to 70 milliliters of balanced salt solution.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
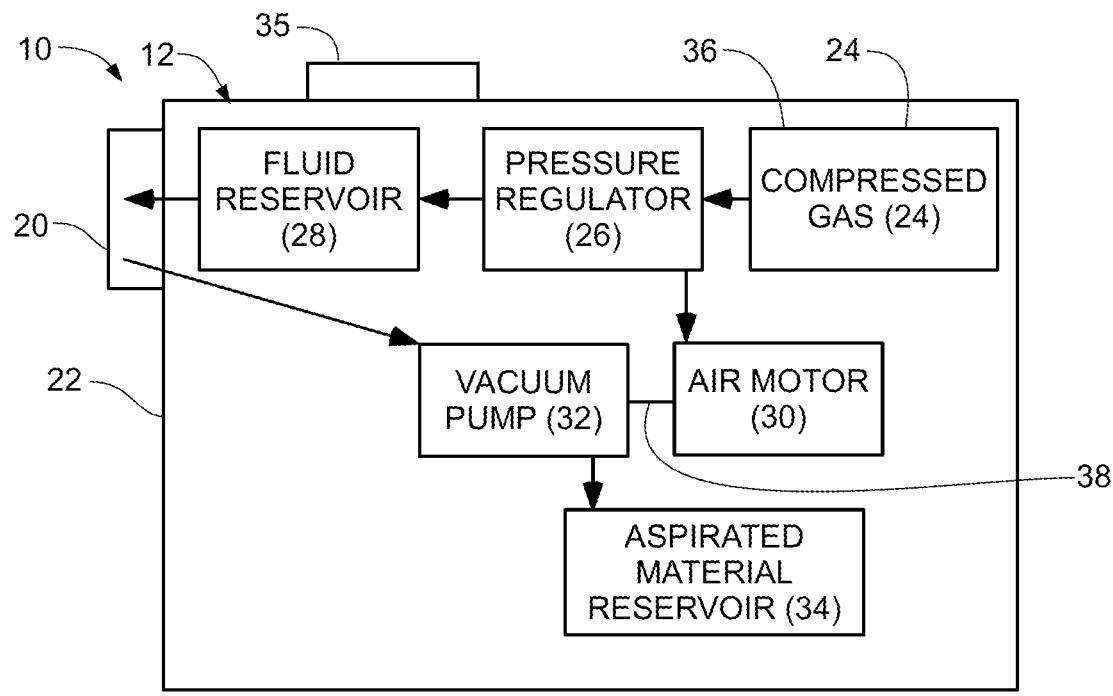
FIG. 1 is a schematic depiction of a power module with an attached lens aspiration module according to an example embodiment of the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIGS. 1-4, according to an example embodiment of the invention, self-contained handheld ophthalmic surgery instrument 10 generally includes power module 12, lens aspiration module 14, vitrectomy module 16 and lens insertion module 18. Power module 12 is coupleable to each of lens aspiration module 14, vitrectomy module 16 and lens insertion module 18 via mating coupler 20. Power module 12 is self-contained and provides operating support for lens aspiration module 14, vitrectomy module 16 and lens insertion module 18 without connection to any outside console.

Referring particularly to FIG. 1, power module 12 generally includes body 22 presenting mating coupler 20 on an outside thereof and further including, compressed gas supply 24, pressure regulator 26, fluid reservoir 28, air motor 30, vacuum pump 32 and aspirated material reservoir 34. Power module 12 further includes control panel 35.

Compressed gas supply 24 includes pressure vessel 36 structured to contain compressed gas such as compressed air. Compressed gas supply 24 is coupled in fluid communication with pressure regulator 26. Pressure regulator 26 controls pressure and flow of compressed gas contained in compressed gas supply 24.

Pressure regulator 26 is further coupled in fluid communication with a fluid reservoir 28 and air motor 30. Pressure regulator 26 is adapted supply compressed gas to air motor 30 at an appropriate pressure and flow rate in order to operate air motor 30. Air motor 30 may be similar to those utilized in dental equipment for example. Pressure regulator 26 is also adapted to supply compressed gas to fluid reservoir 28 at an appropriate pressure to cause fluid contained in fluid reservoir 28 to flow to provide replacement fluid to compensate for fluids removed from the eye during surgical procedures. Accordingly, pressure regulator 26 may be adjustable dependent upon whether power module 12 is utilized with a lens aspiration module 14 vitrectomy module 16 or lens insertion module 18. Adjustments may be accomplished manually or automatically based on the coupling of the appropriate module to power module 12.

Fluid reservoir 28 is in fluid communication with pressure regulator 26 as well as with mating coupler 20. Fluid reservoir 28 is adapted to contain a supply of a fluid for replacing high fluids that are removed during the eye surgery process. According to example embodiments of the invention, fluid reservoir 28 may have a volume of 50 to 70 mL. Fluid reservoir 28 is pressurized via pressure regulator 26 in to provide fluid to the eye at an appropriate volume and flow rate to compensate for fluid removed during surgery by, for example aspiration.

Vacuum pump 32 is mechanically coupled to air motor 30 via, for example, driveshaft 38. Vacuum pump 32 may for example include a venturi pump, a turbine pump or a piston pump.

In the case of a venturi pump, driveshaft 38 is not utilized. Instead, compressed gas is utilized to create a relative vacuum by the venturi principle as is known to those skilled in the art. In the case of a turbine pump or piston pump, driveshaft 38 transmits power from air motor 32 to vacuum pump 32. Vacuum pump 32 is structured and adapted to provide a sufficient level of vacuum to aspirate material from lens aspiration module 14 or vitrectomy model 16.

Vacuum pump 32 is coupled in fluid communication with aspirated material reservoir 34. Aspirated material reservoir 34 is structured and adapted to receive aspirated material that may arise from the eye during surgical procedures via a lens aspiration module 14 or vitrectomy module 16. Aspirated material reservoir 34 has a sufficient volume to receive and contain aspirated material expected to be received therein during a normal procedure. Aspirated material reservoir 34 may be appropriately vented to the ambient atmosphere to allow for the displacement of air therein. According to another example embodiment of the invention, aspirated material reservoir may be located between vacuum pump 32 and mating coupler 20 so that aspirated material may be drawn into aspirated material reservoir 34 via negative pressure.

Control panel 35 is in controlling communication with compressed gas supply 24, pressure regulator 26, fluid reservoir 28, air motor 30 and/or vacuum pump 32. Control panel may include valves, electromechanical controllers and electrical or electronic controllers as known to those skilled in the art that control the functions of self-contained ophthalmic surgery instrument 10.

Figure 2:
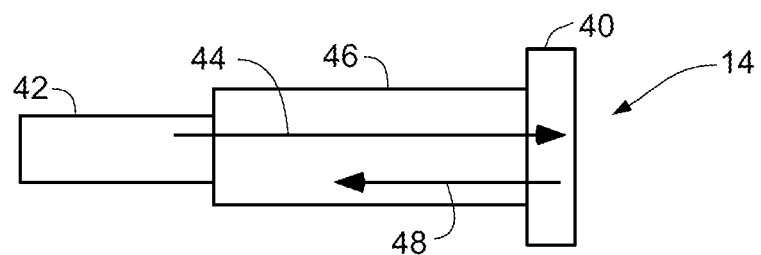
FIG. 2 is a schematic depiction of a lens aspiration module according to an example embodiment of the invention.

Referring now to FIG. 2, lens aspiration module 14 generally includes coupler 40, aspiration cannula 42, aspiration conduit 44, irrigation sleeve 46 and irrigation conduit 48.

Coupler 40 is structured and adapted to be attached to mating coupler 20 of power module 12. Aspiration cannula 42 is coupled to aspiration conduit 44 which in turn is in fluid communication with vacuum pump 32 and/or aspirated material reservoir 34. Coupler 40 is structured so that when it is coupled to mating coupler 20, fluid communication is established between aspiration conduit 44 and vacuum pump 32 or aspirated material reservoir 34. Coupler 40 is further structured so that irrigation conduit 48 is placed in fluid communication with fluid reservoir 28. Aspiration cannula 42 is of an appropriate size to receive fragments of the crystalline lens to be aspirated therethrough. The size of aspiration cannula 42 is determined in part by the expected size of lens fragments to be aspirated. Irrigation sleeve 46 is of an appropriate size to provide a flow of liquid such as balanced salt solution or viscoelastic therethrough to replace fluid aspirated from the eye during surgery because of leakage or aspiration. It may be required that irrigation sleeve 46 be of a different, likely larger, size to accommodate viscoelastic rather than balanced salt solution if viscoelastic is used.

Figure 3:
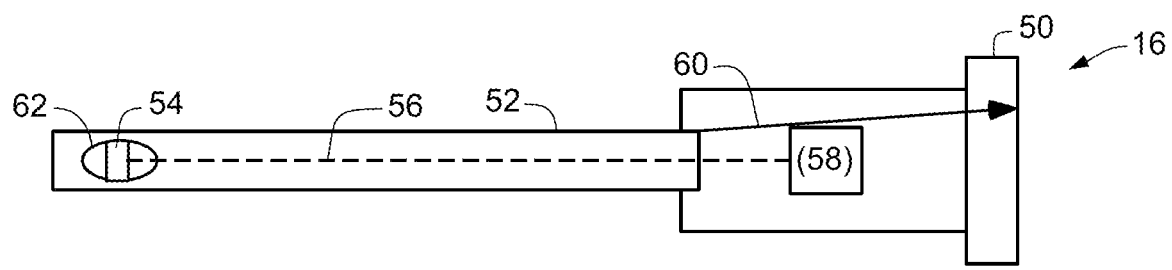
FIG. 3 is a schematic depiction of a vitrectomy module according to an example embodiment of the invention.

Referring now to FIG. 3 vitrectomy module 16 generally includes vitrectomy coupler 50, vitrectomy cannula 52, vitrectomy cutter 54 and cutter oscillator 56. Vitrectomy coupler 50 is adapted to couple in fluid communication with vacuum pump 32 and/or aspirated material reservoir 34. Vitrectomy coupler 50 may further be adapted to couple in fluid communication with pressure regulator 26. Vitrectomy coupler 50 may further house oscillator motor 58. In this case oscillator motor 58 can be coupled with pressure regulator 26. Oscillator motor 58 is operably coupled with cutter oscillator 56. Vitrectomy coupler 50 may also include vitrectomy aspiration conduit 60. Vitrectomy cannula 52 is in operable fluid communication with vitrectomy aspiration conduit 60 which when coupled is in further fluid communication with vacuum pump 32 and/or aspirated material reservoir 34.

Vitrectomy cutter 54 is located within vitrectomy cannula 52 proximate to cannula aperture 62. Cannula aperture 62 has edges in close fitting apposition to vitrectomy cutter 54. Vitrectomy cutter 54 is shiftable within vitrectomy cannula 52 for a distance approximating a length of cannula aperture 62.

Figure 4:
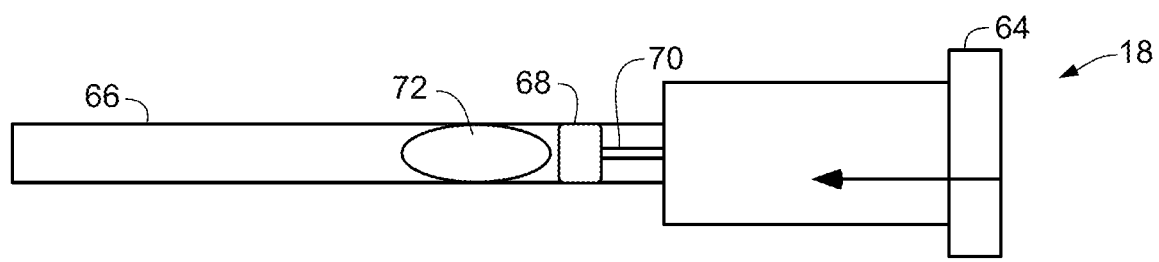
FIG. 4 is a schematic depiction of a lens insertion module according to an example embodiment of the invention.

Referring now particularly to FIG. 4, lens insertion module 18 generally includes lens insertion coupler 64, lens insertion cannula 66, lens insertion piston 68 and lens insertion connecting rod 70. Rolled or folded intraocular lens 72 is also depicted within the lens insertion cannula 66. Lens insertion coupler 64 is adapted to be coupled to mating coupler 20 and in fluid communication with pressure regulator 26 or fluid reservoir 28. Lens insertion piston 68 and lens insertion connecting rod 70 are structured to be advanced by application of pressure. Pressure may be supplied pneumatically via pressure regulator 26 or hydraulically via fluid reservoir 28. Lens insertion piston 68 is slidably advanceable within lens insertion cannula 66 thereby advancing intraocular lens 72 through and ultimately out of lens insertion cannula 66 into an eye.

Example embodiments of the invention further include a method of performing ocular surgery. An example method includes coupling at least one module that facilitates performance of an eye surgery task to a self-contained hand holdable power module that is not coupled to a console; inserting at least one portion of the at least one module into an eye; performing the eye surgery task; and removing then the at least one portion of the at least one module the eye.

The method of performing ocular surgery may further include selecting or making the at least one module to comprise a lens aspiration module, the lens aspiration module including a module coupler structured to operably attach to the self-contained hand holdable power module via a mating coupler, a lens aspiration tube and an irrigation sleeve; and aspirating fragments of a crystalline lens from the eye by application of the lens aspiration module.

The method of performing ocular surgery may further include selecting or making the at least one module to comprise a vitrectomy module including a module coupler structured to operably attached to operably attach to the self-contained hand holdable power module via a mating coupler, a cutting probe, an aspiration portion and a fluid replacement portion; and performing a vitrectomy by application of the vitrectomy module.

The method of performing ocular surgery may further include selecting or making the at least one module to comprise an IOL insertion module including a module coupler structured to operably attached to operably attach to the self-contained hand holdable power module via a mating coupler, a cannula structure that is structured to receive a foldable or rolled IOL therein and a slide or plunger structure that is structured for sliding movement within the cannula structure whereby the foldable or rolled IOL can be advanced through the cannula structure; and inserting an IOL into the eye by application of the IOL insertion module.

The method of performing ocular surgery may further include supplying viscoelastic solution into the eye instead of a balanced salt solution via an irrigation sleeve.

The method of performing ocular surgery may further include supplying the viscoelastic solution into the eye in a volume of less than 10 milliliters or less than 5 milliliters.

The method of performing ocular surgery may further include dividing a crystalline lens of the eye into multiple fragments by application of femtosecond laser energy.

In operation, at least one of lens aspiration module 14, vitrectomy module 16 and lens insertion module 18 is coupled to power module 12 via mating coupler 20. Upon coupling, compressed gas supply 24 vacuum pump 32 and aspirated material reservoir 34 as well as fluid reservoir 28 are coupled in fluid communication with lens aspiration module 14, vitrectomy module 16 or lens insertion module 18 as appropriate. This aspect will be further discussed below.

Once the one of lens aspiration module 14, vitrectomy module 16 and lens insertion module 18 is coupled to power module 12 an operating surgeon may grip power module 12 in a hand such that control panel 35 may be manipulated by the operating surgeon's fingers. Alternately, controlled panel 35 may be remotely located in and controlled by for example, a foot pedal (not shown).

If lens aspiration module 14 is coupled to power module 12 via mating coupler 20 and coupler 40, aspiration cannula 42 is coupled to aspirated material reservoir 34 and vacuum pump 32 so that negative pressure can be applied to aspiration cannula 42. Irrigation sleeve 46 is coupled via irrigation conduit 48 with fluid reservoir 28 so that fluid can be supplied under pressure through irrigation sleeve 46. Fluid may include for example balanced salt solution or viscoelastic. As mentioned above the application of viscoelastic in the lens aspiration process may reduce the volume of liquid required substantially to as little as a few milliliters.

An operating surgeon then manipulates aspiration cannula 42 to be placed in contact with fragments of the crystalline lens of the eye that have previously been created, for example, by the application of femtosecond laser energy to section the crystalline lens of the eye. Because of the vacuum or negative pressure present in aspiration cannula 42 lens fragments are then drawn through aspiration cannula 42 then through aspiration conduit 44 into aspirated material reservoir 34. Lens fragments are then held in aspirated material reservoir 34 for later disposal. Depending upon the design of example embodiments of the invention aspirated material reservoir 34 may either follow or precede vacuum pump 32. As aspiration of lens fragments is accomplished fluid from fluid reservoir 28 is directed through irrigation conduit 48 and then through irrigation sleeve 46 into the eye of the patient and to replace fluid removed by aspiration. This keeps the anterior chamber of the eye from collapsing due to the aspiration of materials from the eye during the procedure. Compressed gas supply 24 is applied to fluid reservoir 28 via pressure regulator 26 in order to supply irrigation fluid via irrigation sleeve 46 at an appropriate pressure and volume. Once all of the crystalline lens fragments armor removed from the eye aspiration cannula 42 an irrigation sleeve 46 are withdrawn from the incision into the eye and the lens extraction procedure is complete.

For vitrectomy procedures, vitrectomy module 16 is coupled to mating coupler 20 of power module 12 via vitrectomy coupler 50.

After coupling an operating surgeon grips power module 12 so that control panel 35 is appropriately manipulable. Vitrectomy cannula 52, including vitrectomy cutter 54, is inserted into the eye and placed in contact with the vitreous body through an incision typically in the pars plana of the sclera. Normally in vitrectomy procedures fluid is replaced in the eye via a separate conduit. Accordingly, fluid replacement may not be activated during a vitrectomy procedure.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of performing ocular surgery, the method comprising:
coupling at least one module that facilitates performance of an eye surgery task to a self-contained hand holdable power module that is not coupled to a console,
thereby coupling the at least one module with access to a compressed gas supply located within the self-contained hand holdable power module, wherein the compressed gas supply is also operably coupled to an aspiration pump;
thereby also coupling the at least one module with access to a fluid reservoir located within the self-contained hand holdable power module, further wherein the fluid reservoir is in fluid communication with a mating coupler such that fluid is supplied under pressure to the mating coupler and thus to the at least one module that facilitates performance of an eye surgery task;
thereby also coupling the at least one module with access to the aspirated material reservoir located within the self-contained hand holdable power module to receive aspirated material from the mating coupler and wherein the aspirated material reservoir is in fluid communication with the aspiration pump; and
controlling operation of the at least one module via a control panel that is in controlling communication with the compressed gas supply, the aspiration pump and the aspirated material reservoir;
inserting at least one portion of the at least one module that facilitates performance of the eye surgery task into an eye;
performing the eye surgery task; and
removing the at least one portion of the at least one module that facilitates performance of an eye surgery task from the eye.

2. The method of performing ocular surgery as claimed in claim 1, further comprising:
selecting or making the at least one module to comprise a lens aspiration module, the lens aspiration module including a module coupler structured to operably attach to the self-contained hand holdable power module via a mating coupler, a lens aspiration tube and an irrigation sleeve; and
aspirating fragments of a crystalline lens from the eye by application of the lens aspiration module.

3. The method of performing ocular surgery as claimed in claim 1, further comprising:
selecting or making the at least one module to comprise a vitrectomy module including a module coupler structured to operably attach to the self-contained hand holdable power module via a mating coupler, a cutting probe, an aspiration portion and a fluid replacement portion; and
performing at least a partial vitrectomy by application of the vitrectomy module.

4. The method of performing ocular surgery as claimed in claim 1, further comprising:
selecting or making the at least one module to comprise an IOL insertion module including a module coupler structured to operably attach to the self-contained hand holdable power module via a mating coupler, a cannula structure that is structured to receive a foldable or rolled IOL therein and a slide or plunger structure that is structured for sliding movement within the cannula structure whereby the folded or rolled IOL can be advanced through the cannula structure; and
inserting an IOL into the eye by application of the IOL insertion module.

5. The method of performing ocular surgery as claimed in claim 1, further comprising supplying viscoelastic solution into the eye instead of a balanced salt solution via an irrigation sleeve.

6. The method of performing ocular surgery as claimed in claim 5, further comprising supplying the viscoelastic solution into the eye in a volume of less than 10 milliliters.

7. The method of performing ocular surgery as claimed in claim 5, further comprising supplying the viscoelastic solution into the eye in a volume of less than 5 milliliters.

8. The method of performing ocular surgery as claimed in claim 1, further comprising dividing a crystalline lens of the eye into multiple fragments by application of femtosecond laser energy prior to aspiration of the multiple fragments from the eye.

* * * * *